Figure 1:
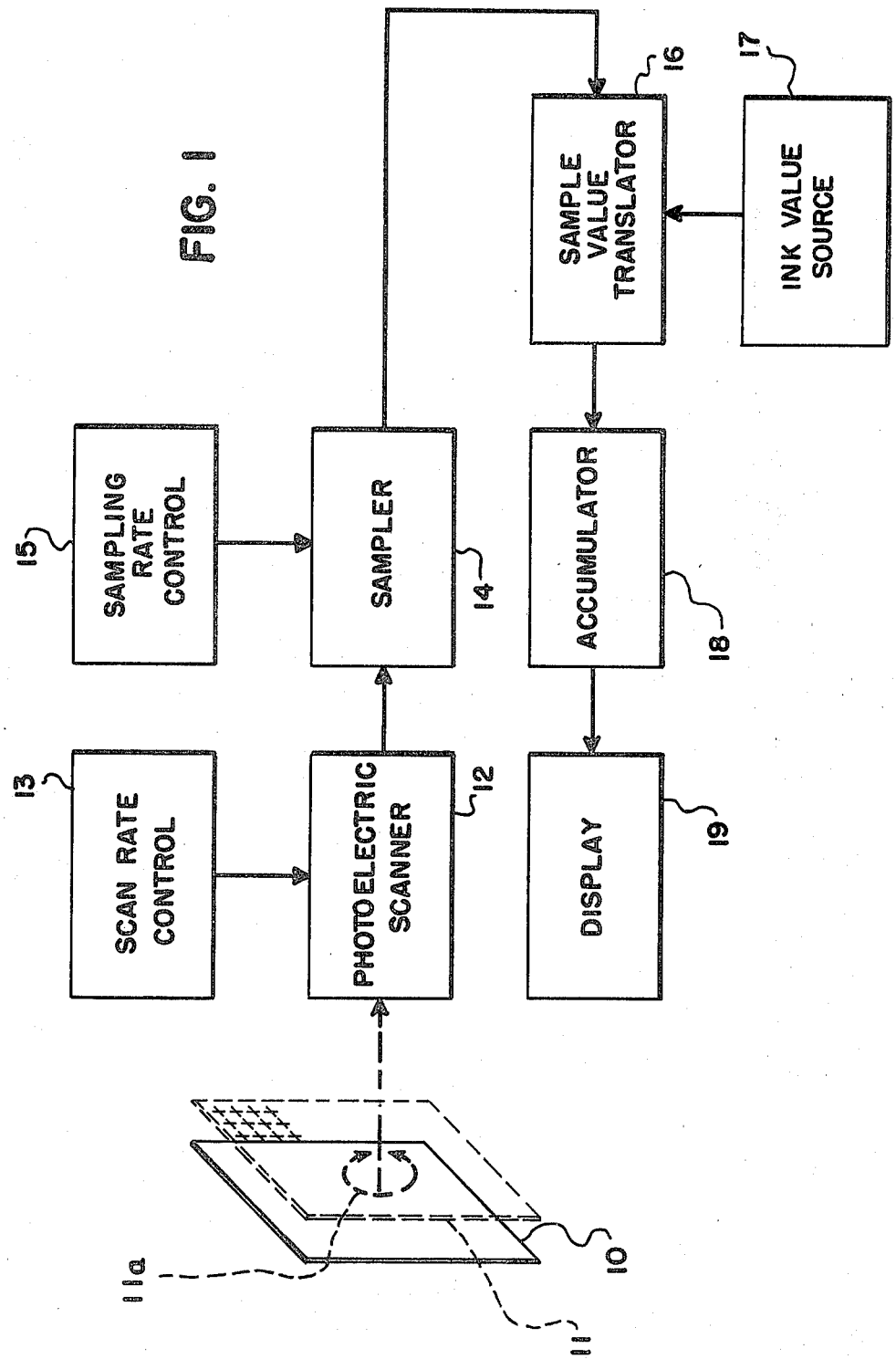

United States Patent [19]

Hoffman

[11] 4,422,765
[45] Dec. 27, 1983

[54] OFF-SET PRINTING INK CONSUMPTION PREDICTION

[76] Inventor: Ernst R. Hoffman, P.O. Box E, Atglen, Pa. 19310

[21] Appl. No.: 179,767

[22] Filed: Aug. 20, 1980

[51] Int. Cl.³ .................... G01N 21/17; G01N 21/84
[52] U.S. Cl. .................................. 356/432; 101/426; 101/DIG. 24; 250/237 G; 356/444; 356/445
[58] Field of Search ................. 356/72, 432, 444–445; 101/DIG. 24, 426, 425; 250/237 G, 559; 358/296; 340/146.3 A, 146.3 G, 146.3 AH

[56] References Cited

U.S. PATENT DOCUMENTS

| | | | |
|---|---|---|---|
| 3,053,181 | 9/1962 | Jorgensen | 356/445 |
| 3,347,131 | 10/1967 | Claver et al. | 356/445 |
| 3,841,215 | 10/1974 | Hasegawa | 101/426 |
| 4,051,458 | 9/1977 | Morton | 350/146.3 AG |
| 4,155,103 | 5/1979 | Gamblin et al. | 250/237 G |

FOREIGN PATENT DOCUMENTS 2012313  7/1979  United Kingdom ....... 101/DIG. 24

OTHER PUBLICATIONS

Ett, A. H. "Elimination of Moire Sampling Errors", IBM Tech. Disc. Bull 3 1970, pp. 1596–1597.

Primary Examiner—William H. Punter
Attorney, Agent, or Firm—Weiser & Stapler

[57] ABSTRACT

Glass screens with different line numbers are used to determine the photoelectric scanning and sampling rates which provide signal samples reliably representative of the density of the off-set image dot structure. Using these rates, the corresponding ink consumption values are determined, totaled over the image, and displayed.

6 Claims, 2 Drawing Figures

OFF-SET PRINTING INK CONSUMPTION PREDICTION

This invention relates to improvements in the techniques which are utilized to predict the consumption of printing ink. More particularly, the invention relates to an improved technique for determining, in advance of printing, how much ink can be expected to be consumed during the subsequent printing of a particular image.

There are many instances, in the printing art, in which it is eminently desirable to be able to predict how much ink can be expected to be consumed in reproducing a particular image.

For example, printing firms are frequently asked, by the originator of the material to be printed, to submit bids for the printing work to be performed. Ink is one of the major factors in the cost of the printing operation. In turn, the quantity of ink required to produce a particular printed image varies widely, depending upon the content of the image. If the image is to have a comparatively "dense" appearance, then more ink will be required than if it is to have a comparatively "light," or pale appearance.

These ink quantity variations can extend over several orders of magnitude.

It is therefore believed to be apparent that wide variations in expected cost, and correspondingly wide variations in bid price, can occur depending upon ink quantity. This places a corresponding premium upon the ability to determine in advance what quantity of ink will be needed. If this quantity is estimated too low, then there is the danger of a bid which is too low, with serious financial repercussions to the printing firm making the bid. If the quantity is estimated too high, then the bid will also be higher than necessary, and this may cause the originator of the material to pay an excessive price for the printing or else cause this particular printing firm to lose the job to another, lower-priced bidder.

Problems such as those briefly described above are currently being further exacerbated by the rapidly rising cost of printing ink, which is a petroleum derivative, and therefore has been following the spiralling cost trend of other petroleum-based products.

Although this problem of reliably predicting ink requirements has long been recognized, completely satisfactory solutions have been lacking.

The most prevalent technique for making the prediction has been a strictly ocular one. An operator would visually examine the original image from which printing plates were subsequently to be made. From this visual examination, and applying past experience in such matters, the operator would then mentally estimate how much ink would be required.

It hardly needs to be pointed out that this represents an exceedingly difficult task. There is a virtually infinite variety of image contents. This variety involves not only variations in density, but also variations in hue for color printing. In addition, different ink which could be used to form the very same ultimate printed image have different characteristics, which require these inks to be used in different quantities. Likewise, different print support materials, e.g. paper, fabric, plastic, all call for applications of different ink quantities.

All this led to a severe lack of reliability in prediction by the ocular technique mentioned above.

A major step forward was taken by the present applicant for patent when he recently introduced an automated technique for performing this prediction.

This involved the following. First there was performed photoelectric line-by-line scanning of the original image from which the actual printing plates were subsequently to be made. The resultant electrical signals, which represent the density of the scanned lines of that original image, were then sampled at periodic intervals, in order to determine their magnitude at each sampling interval. These magnitudes were then "translated" into corresponding values of printing ink quantity required to achieve the corresponding image density in the ultimate printed image. Finally, these ink quantity-representative values were accumulated or totalled for all the samples derived from a particular image. This total then corresponded to the total amount of ink required for the printing of that image.

In this way, the virtually impossible demands previously imposed upon the estimating skills of the human operator were essentially eliminated and, indeed, the prediction reliability was tremendously increased.

A public description of the aforementioned new technique for ink consumption prediction may be found in an article entitled Ink Consumption Scanner by Carl M. Metash, which appeared in the June 1979 issue of Gravure Technical Association Magazine.

In gaining experience with this new technique, it was further recognized that, occasionally, the reliability of prediction which normally prevailed would break down and as a result, a prediction of ink consumption for a given image would be made which was wide of the mark, even though the equipment used was functioning normally, and was able to provide predictions with the accustomed reliability for different images.

It was then recognized that the characteristic feature of those images for which the prior new technique was not always reliable was that they were images ultimately destined for off-set printing. In contrast, for images ultimately destined for gravure printing, this prior new technique did not appear to suffer from the same lapses in reliability.

Accordingly, it is an object of the present invention to provide an automated technique for predicting printing ink requirements which does not suffer from the occasional lapses noted above.

It is another object to provide such a technique which is applicable to images ultimately destined to be reproduced by off-set printing.

It is still another object to provide such a technique which is applicable to original images which have already been subjected to screening before the prediction is to be automatically performed.

These and other objects which will appear are achieved in accordance with the present invention by preceding the performance of my above-described automated prediction technique with a preliminary analysis of the dot-structure of the original image. This analysis is to determine the rates at which the subsequent photoelectric line scanning of the image and sampling of the electrical signal produced by the scanning is to be performed. These rates are then adjusted accordingly, and my automated technique then proceeds, free from the lapses in reliability which could otherwise occur.

Figure 2:
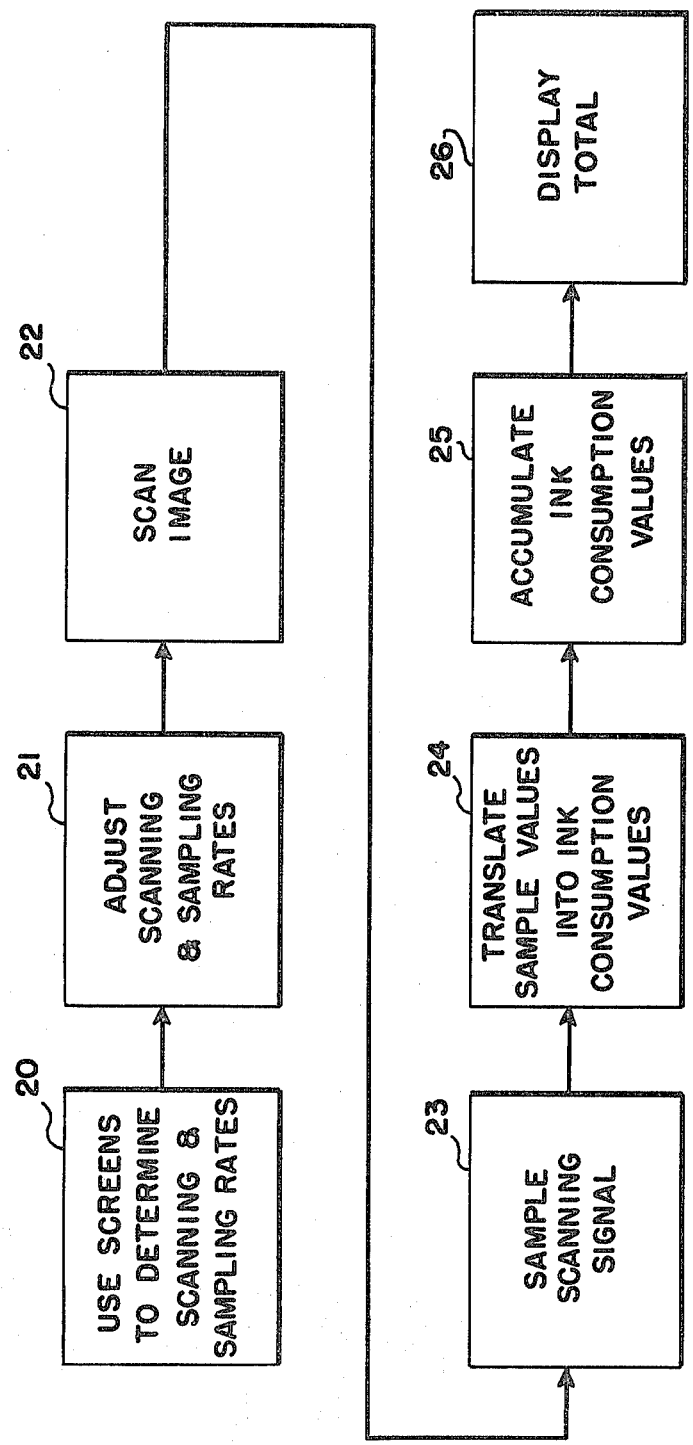

For further details, reference is made to the discussion which follows, in light of the accompanying drawings, wherein, FIG. 1 is a block-diagram illustration of equipment utilized to practice the present invention; and FIG. 2 is a flow diagram of the steps constituting the inventive technique.

Referring to FIG. 1, this shows, in perspective, sheet 10 which bears the original image to be processed in accordance with my new technique.

Overlying sheet 10 is another sheet 11 which is shown in broken lines because it is present only during part of the procedure embodying the present invention. This sheet 11 does not bear an image to be reproduced. Rather, sheet 11 is a glass conventional screen such as is used in printing technology. A photoelectric scanner 12 is provided, which is constructed and arranged so as to scan line-by-line the image-bearing sheet 10. Control means 13 is provided for adjusting the rate at which this line-by-line scanning operation is performed. Through the operation of the photoelectric scanner 12 at the rate determined by control means 13, there is produced at the output of the scanner 12 an electrical signal which varies in intensity in accordance with the density of the contemporaneously scanned lines of the image on sheet 10. This signal from scanner 12 is then periodically sampled in a sampler 14. The rate at which this sampling operation is performed is subject to variation by sampling rate control means 15. As a result of the sampling operation, the electrical signal which represents the density of the image lines scanned by photoelectric scanner 12 is broken up into separate signal portions or samples, representing the density of line segments, or dots scanned by the photoelectric scanner 12 on image-bearing sheet 10. These density-representative signal samples from sampler 14 are then supplied to a sample value translator 16. Also supplied to this sample value translator 16, from a source 17, are signals which vary as a function of the relationship between various image densities and the quantity of printing ink which is necessary to produce an image of that particular density during printing. For each image density-representative signal sample from sampler 14, translator 16 selects the ink quantity-representative value from source 17. The ink consumption-representative signal thus selected is then transmitted to accumulator 18. In accumulator 18 there are accumulated, or added together, all of the signals from source 17 thus selected consecutively over the entire image-bearing sheet 10. A running total of these accumulated values may be visually displayed on display 19 or, at least, the final total so accumulated from scanning the entire image-bearing sheet 10 is so displayed.

The apparatus of FIG. 1 is utilized in accordance with the present invention in the manner described further below and as also illustrated diagrammatically in the flow diagram of FIG. 2.

As the initial step, represented in rectangle 20 of FIG. 2, one or more conventional glass screens are used to determine the scanning and sampling rates of the equipment of FIG. 1. To that end, the image-bearing sheet 10 of FIG. 1 has placed upon it a conventional glass screen such as shown at 11 in FIG. 1. If the screen number which was used previously to produce the screened off-set image on sheet 10 is known, then a screen 11 which a somewhat higher number (i.e. a greater number of lines per inch) should be used. This last screen 11 is then pivoted back and forth, with respect to the image-bearing sheet 10 as indicated by the two-headed broken line arrow 11a in FIG. 1. This causes moiré patterns to develop. The first such screen 11 is then replaced with a higher numbered glass screen and the back and forth pivoting is repeated. A third and possibly other, still higher numbered glass screens 11, are similrly utilized in sequence. As different glass screens 11 are utilized in this manner, different moiré patterns will be observed. In practice, it develops that one of the glass screens 11 in this series will produce a perceptibly finer and therefore less conspicuous moiré pattern than the others. The number of lines per inch which characterizes that particular screen 11 is then utilized to determine the screening and sampling rates to be employed in the equipment of FIG. 1, when operated in accordance with the present invention.

In particular, the scanning rate of the photoelectric scanner 12 is adjusted by scan rate control means 13 to provide a pattern of scanning lines across the image-bearing sheet 10 which generally equals the line pattern of the particular glass screen 11. Likewise, the sampling rate of sampler 14 is adjusted by sampling rate control means 15 so that along each scanning line, separate samples are taken at intervals which correspond generally to the line spacing of the same glass screen 11. The foregoing is represented in FIG. 2 by rectangle 21 in the flow chart.

Having made these adjustments, the image on sheet 10 is then scanned (rectangle 22 in FIG. 2), and the scanning signal is sampled (rectangle 23 in FIG. 2). It will be understood that during these scanning and sampling operations, the screen 11 is not present. Rather, the photoelectric scanning operation is performed upon the image-bearing sheet 10 directly, without any intervening glass screen 11. At the output of sampler 14 of FIG. 1, there will thus be present a sampled scanning signal (see rectangle 23 in FIG. 2) which has separate, consecutive, electrical signal values representing the density values of the image on sheet 10 as viewed through the particular glass screen 11 which was used to determine the scanning and sampling rates. Thus, the photoelectric scanner 12 and sampler 14 can be thought of as providing a "virtual screen" which electronically decomposes the image on sheet 10 into a series of consecutive electrical signals respectively representing the density values of different points or dots in the image.

As indicated by rectangle 24 of FIG. 2, these electrical signal samples representing image density are then translated into corresponding signal values representing the amount of ink which would be necessary under the particular circumstances to print an image having that same density. In FIG. 1, as previously pointed out, this is accomplished by means of translator 16 supplied with both the signal from sampler 14 and the signal from source 17.

As indicated by rectangle 25 in FIG. 2, the individual ink consumption values corresponding to the sampled points in the image on sheet 10 are then accumulated over the entire image. This is accomplished by accumulator 18 of FIG. 1. Finally, the total of these accumulated values is displayed as indicated in rectangle 26 of FIG. 2. This display is accomplished by display means 19 of FIG. 1.

It is now believed to be apparent that the essential differences between the present invention and my previously mentioned new technique for predicting ink consumption which is referenced in the Gravure Technical Association Magazine mentioned above, is that the present invention involves making an initial determination of the requirements of the particular image to be processed with respect to scanning and sampling rates and then adjusting these rates accordingly. This is predicated on the recognition that the fixed scanning and sampling rates employed in my prior new technique is inherently incompatible with off-set image processing. More particularly, I have recognized that the interaction between a particular fixed scanning and sampling rate, and many of the possible dot patterns which arise from the use of various screens in the production of off-set images, create sampled signal values which do not faithfully represent the density of the off-set image. In the extreme case, it is even possible for all of the signal samples to be taken at intervals which correspond to those points in the image which have no image-representing dots at all, but rather which lie in the spaces between image dots. In that extreme case, my prior new technique would provide an indication of essentially zero image density and, correspondingly, there would be made a prediction of minimal ink consumption. This would not be at all in accordance with reality, since the image density might actually be quite high and therefore require a large ink consumption.

Although such extreme cases would be rare, nevertheless the danger exists that they may occur. Moreover, and more importantly, if fixed scanning and sampling rates are used, there will be a strong tendency for what amount to electronic moiré effects to be produced. What this means is that the sampling in some portions of the image will indeed be performed at intervals corresponding to the scanning of the actual image dots, while in other portions of the image the sampling will be performed at intervals corresponding to the scanning of blank portions (between dots). Correspondingly, the image density values represented by these two different sets of samples will be correct and incorrect, respectively. The overall correctness of the indication provided by the prediction technique using fixed rates is therefore impaired to that degree. Moreover, since different portions of an image will frequently differ in density from each other, there arises the additional problem that the image portions which are correctly represented by samples may happen to be the image portions of low density, while those incorrectly represented may happen to be the image portions of high density, or vice versa. In either case, this would further distort the prediction of total ink consumption. In any event, the ink consumption prediction should not be dependent on the chance distribution of properly and improperly sampled image portions.

All of the foregoing problems are ingeniously avoided by the recognition of their source and by their treatment in accordance with the present invention.

Taken individually, the components of the equipment which is used to practice my invention (FIG. 1) and to perform the steps represented in the flow diagram of FIG. 2 are well known and may take any of a variety of conventional forms.

For example, the glass screens 11 are, of course, conventional pieces of apparatus in the printing art.

The remainder of the equipment shown in FIG. 1, with certain exceptions noted below, may be of the same form as illustrated and described in the above-mentioned Gravure Technical Association Magazine article. In that article, the Hell scanner (model C286) is not specifically intended, nor described, to be controllable with respect to scanning rate. However, as is well known and shown in the article, this scanner consists of a photoelectric scanning head which traverses axially along a rotating cylinder. The image-bearing sheet is wrapped around that cylinder, each scanning line being formed by one rotation of the cylinder and consecutive scanning lines being created by the axial displacement of the scanning head. It is apparent that, by conventional means the speed of rotation of the cylinder and/or the axial movement of the scanning head can be controlled, and the scanning rate thereby adjusted as needed.

Also in the Gravure Technical Association Magazine article, the sampling rate is not intended nor described as being subject to control. Rather, a fixed sampling rate 220 per inch of cylinder circumference is described. However, the sampling operation is performed electronically in conventional manner, and it is apparent that the rate of such electronic sampling operation can be adjusted as needed by conventional means.

I claim:

1. In the method of predicting the printing ink consumption of an off-set image, which method includes the steps of photoelectrically scanning the screened image from which the off-set image is to be produced along a linear scanning path, periodically sampling the resulting electrical signal, utilizing the signal samples to produce signal values representing the corresponding ink consumption requirements, and totaling and displaying the so-produced values, the improvement which comprises analyzing the screened image to determine the scanning and sampling rates which will produce samples reliably corresponding to the density of the image dots, and performing the scanning and sampling at the rates so determined, the analyzing comprising overlaying the screened image consecutively with glass screens having different line numbers, pivoting each screen back and forth to create moiré patterns through interaction between the screen and the image, and determining the least conspicuous moiré pattern so produced.

2. The method of claim 1 further comprising establishing the scanning and sampling rates so that they produce signal samples which correspond to portions of the screened image spaced in the same manner as by the glass screen which was determined to produce the least conspicuous moiré pattern.

3. The method of claim 1 wherein the glass screens are all selected to have a line number which is greater than that of the screen by which the screened image was produced.

4. In a system for predicting the printing ink consumption of an off-set image, which system includes means for photoelectrically scanning the screened image from which the off-set image is to be produced along a linear scanning path, means for periodically sampling the resulting electrical signal, means for utilizing the signal samples to produce signal values representing the corresponding ink consumption requirements, and means for totaling and displaying the so-produced values, the improvement which comprises means for analyzing the screened image to determine the scanning and sampling rates which will produce samples reliably corresponding to the density of the image dots, and means for controlling the scanning and sampling means to perform the scanning and sampling at the rates so determined, the analyzing means comprising a plurality of glass screens having different line numbers, said screens being adapted to overlay the screened image consecutively, and being adapted to be pivoted back and forth to create moiré patterns through interaction between the screen and the screened image, whereby the least conspicuous moire pattern so produced becomes determinable.

5. The system of claim 4 wherein the scanning and sampling means are controlled by the scanning and sampling control means so that they produce signal samples which correspond to portions of the screened image spaced in the same manner as by the glass screen which was determined to produce the least conspicuous moiré pattern.

6. The system of claim 4 wherein the glass screens have line numbers which are greater than that of the screen by which the screened image was produced.

* * * * *